(12) United States Patent
Vandewalle

(10) Patent No.: US 9,433,493 B2
(45) Date of Patent: Sep. 6, 2016

(54) TISSUE CONTACTING MEMBER

(71) Applicant: Biomet Sports Medicine, LLC, Warsaw, IN (US)

(72) Inventor: Mark V. Vandewalle, Pierceton, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 431 days.

(21) Appl. No.: 14/071,331

(22) Filed: Nov. 4, 2013

(65) Prior Publication Data

US 2015/0127027 A1    May 7, 2015

(51) Int. Cl.
*A61B 17/08* (2006.01)
*A61F 2/08* (2006.01)

(52) U.S. Cl.
CPC ...... *A61F 2/0811* (2013.01); *A61F 2002/0829* (2013.01); *A61F 2002/0858* (2013.01); *A61F 2002/0882* (2013.01); *A61F 2002/0888* (2013.01)

(58) Field of Classification Search
CPC .............. A61F 2/0811; A61F 2002/0876; A61F 2002/0888; A61F 2002/0882; A61F 2002/0823; A61F 2002/0841; A61F 2002/0829; A61F 2002/0858; A61F 2002/0864
See application file for complete search history.

(56) References Cited

U.S. PATENT DOCUMENTS

| 5,906,617 | A * | 5/1999 | Meislin | A61B 17/1146 606/331 |
|---|---|---|---|---|
| 6,056,751 | A * | 5/2000 | Fenton, Jr. | A61B 17/0401 606/151 |
| 6,248,108 | B1 * | 6/2001 | Tormala | A61B 17/8625 411/533 |
| 6,464,706 | B1 * | 10/2002 | Winters | A61B 17/0401 606/99 |
| 6,562,044 | B1 * | 5/2003 | Cooper | A61F 2/0811 606/300 |
| 6,592,609 | B1 * | 7/2003 | Bonutti | A61B 17/0401 606/232 |
| 2002/0022861 | A1 * | 2/2002 | Jacobs | A61B 17/064 606/216 |
| 2003/0171811 | A1 * | 9/2003 | Steiner | A61L 27/386 623/13.17 |
| 2003/0225424 | A1 * | 12/2003 | Benderev | A61B 17/0401 606/151 |
| 2005/0197699 | A1 * | 9/2005 | Jacobs | A61F 2/0811 623/13.14 |
| 2006/0029633 | A1 * | 2/2006 | Kaiser | A61F 2/08 424/422 |
| 2007/0123984 | A1 | 5/2007 | Hodorek | |
| 2011/0040339 | A1 * | 2/2011 | Solomon | A61B 17/8605 606/312 |
| 2012/0209401 | A1 * | 8/2012 | Euteneuer | A61F 2/0063 623/23.72 |
| 2013/0096678 | A1 * | 4/2013 | Denham | A61B 17/0401 623/13.14 |

FOREIGN PATENT DOCUMENTS

FR    2638349 A1    5/1990

* cited by examiner

Primary Examiner — Jonathan Miles
(74) Attorney, Agent, or Firm — Schwegman Lundberg & Woessner, P.A.

(57) ABSTRACT

A contacting or friction pad for engaging a member. The member may be a soft tissue portion to be fixed to a bone using the contacting member. A further fixation member may be used to fix the contacting pad and the member to the bone.

13 Claims, 7 Drawing Sheets

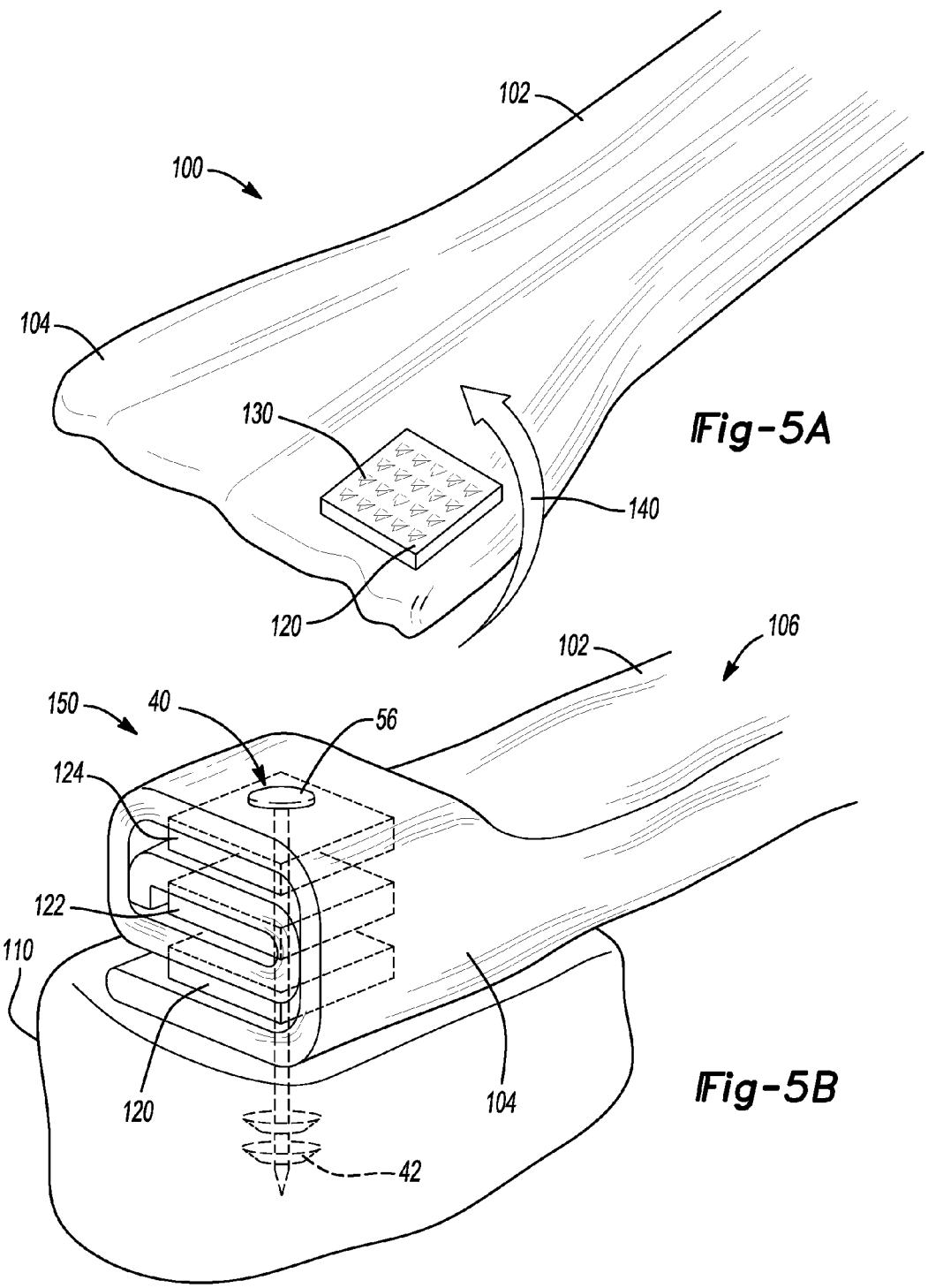

TISSUE CONTACTING MEMBER

FIELD

The subject disclosure relates to a contacting system and/or member, and particularly to a friction, contacting, and/or fixation member able to be positioned relative to a soft tissue portion for reinforcement and/or fixation to a bone member.

BACKGROUND

This section provides background information related to the present disclosure which is not necessarily prior art.

Generally, in a surgical procedure soft tissue can be positioned or fixed relative to a portion of the anatomy, such as a bone portion. This soft tissue can be fixed with various techniques, including an anchor system, screw fixation system, and other appropriate fixation or anchoring mechanisms. The soft tissue, however, is generally fixed to a single member that is anchored to a boney portion for fixation of a soft tissue during and after the surgical procedure. The soft tissue, however, is generally fixed at a single fixation point. For example, a single pin or nail can pierce or contact the soft tissue for the single point of fixation with a fixation member at an end of a soft tissue portion.

SUMMARY

This section provides a general summary of the disclosure, and is not a comprehensive disclosure of its full scope or all of its features.

A soft tissue portion can be fixed to a bone using a contacting member that can include a relatively large surface area. The contacting member can also be referred to as a friction pad or member. The contacting member can include a surface that is much larger than its thickness and/or a thickness of the soft tissue being fixed. The pad or the soft tissue contacting member can provide a large surface area that can be greater than a shaft of a fixation nail or screw to fix soft tissue relative to a second portion, such as a boney portion.

The soft tissue contacting pad can be positioned between two or more layers of soft tissue. The layers of soft tissue can be layered as part of a continuous portion of soft tissue. The soft tissue portion can be folded upon itself, as discussed further herein. The soft tissue can also be naturally connected at a proximal or distal location. Thus, the soft tissue can be reconnected to a proximal humerus for repairing a rotator cuff tear. Additionally, the soft tissue contacting pad can be positioned between various layers of other selected soft tissue portions, such as an anterior cruciate ligament graft.

The soft tissue fixation pad can include a surface area that is generally equivalent to a portion contacting soft tissue at an end or other appropriate portion of the soft tissue. The soft tissue fixation pad can further include a surface that is roughened and/or not smooth relative to the soft tissue position. Further, a fixation member can pass through the soft tissue and/or the soft tissue contacting pad to assist in fixing the soft tissue fixation pad and/or the soft tissue relative to a second structure, such as a bone portion. Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 5A is a detail view of a soft tissue portion and one friction pad;

FIG. 5B is a detail view of a portion of a fixation region of a soft tissue with friction pads, according to various embodiments;

Corresponding reference numerals indicate corresponding parts throughout the several views of the drawings.

DETAILED DESCRIPTION

Example embodiments will now be described more fully with reference to the accompanying drawings.

Figure 1A:
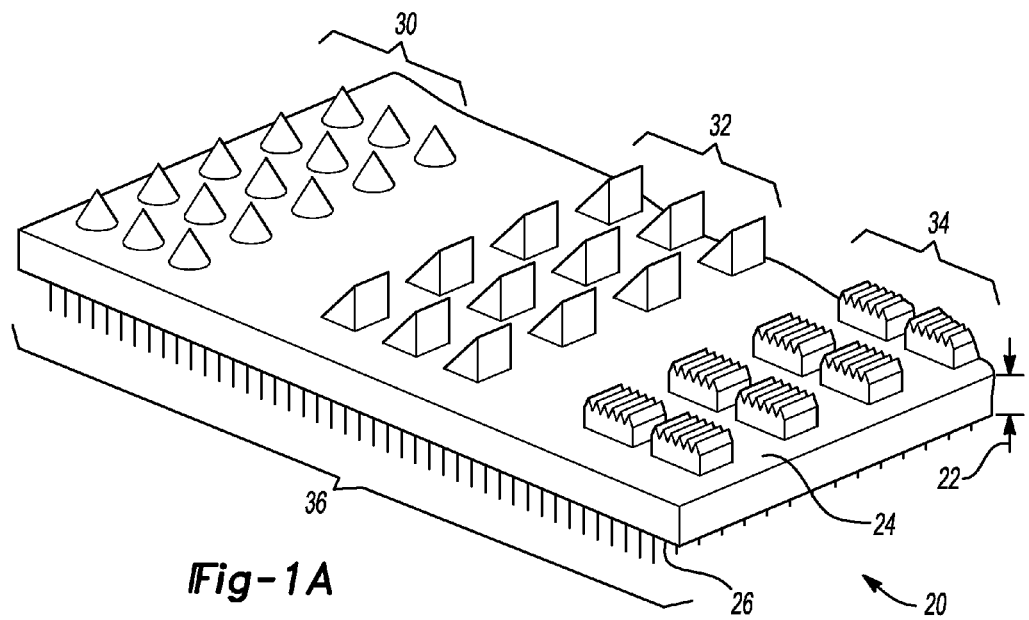
FIG. 1A is a view of a first side of a contacting or friction pad, according to various embodiments.

With reference to FIG. 1A, a soft tissue fixation pad 20 is illustrated. The soft tissue fixation pad 20 can also be referred to as a soft tissue contacting member or pad. The soft tissue fixation pad 20 can include a selected thickness 22 which may vary depending upon an application and/or the position of fixation pad 20 relative to an anatomy of a subject, such as a human patient. For example, fixation of a ligament, tendon, and/or muscle portion relative to a proximal humerus may allow for a section of the soft tissue fixation pad 20 to have a thickness 22 of any appropriate thickness.

The thickness 22 of the soft tissue fixation pad 20 may be selected, according to various embodiments, to be between about 0.1 millimeter and about 1 centimeter, including about 0.2 millimeter to about 10 millimeters, and further including about 0.2 mm to about 0.3 mm. As discussed herein, the surface area of at least one surface of the fixation pad 20 can be greater than the thickness or edge area.

The fixation pad 20 may be provided to reinforce or strengthen a fixation region or zone, as discussed further herein. Various materials can be appropriately selected to provide stiffness and strength. For example, biocompatible materials including stainless steels, titanium, cobalt chromium alloys, etc. can be machined or worked into appropriate shapes and/or thicknesses. Further, selected polymer materials may also be formed in appropriate sizes for engaging the tissue.

The friction pad 20 can include a surface area, such as any appropriate surface area that may be required or selected for a selected area or selected procedure. The surface area can be defined by a first surface 24 and/or a second surface 26. For example, both of the surfaces 24, 26 can be the same area or different areas. Also, the surface area can be selected for various purposes, a rotator cuff attachment, anterior cruciate ligament (ACL) attachment, selected knee and/or hip associated ligament attachment, and other appropriate soft tissue procedures may require or select different areas for contact with the soft tissue. Accordingly the surface area of the friction pad 20 can be selected for procedure or location, such as selected by a user. The friction pad 20 may also be provided in various sizes, such as in a kit for selection by a user.

Figure 4:
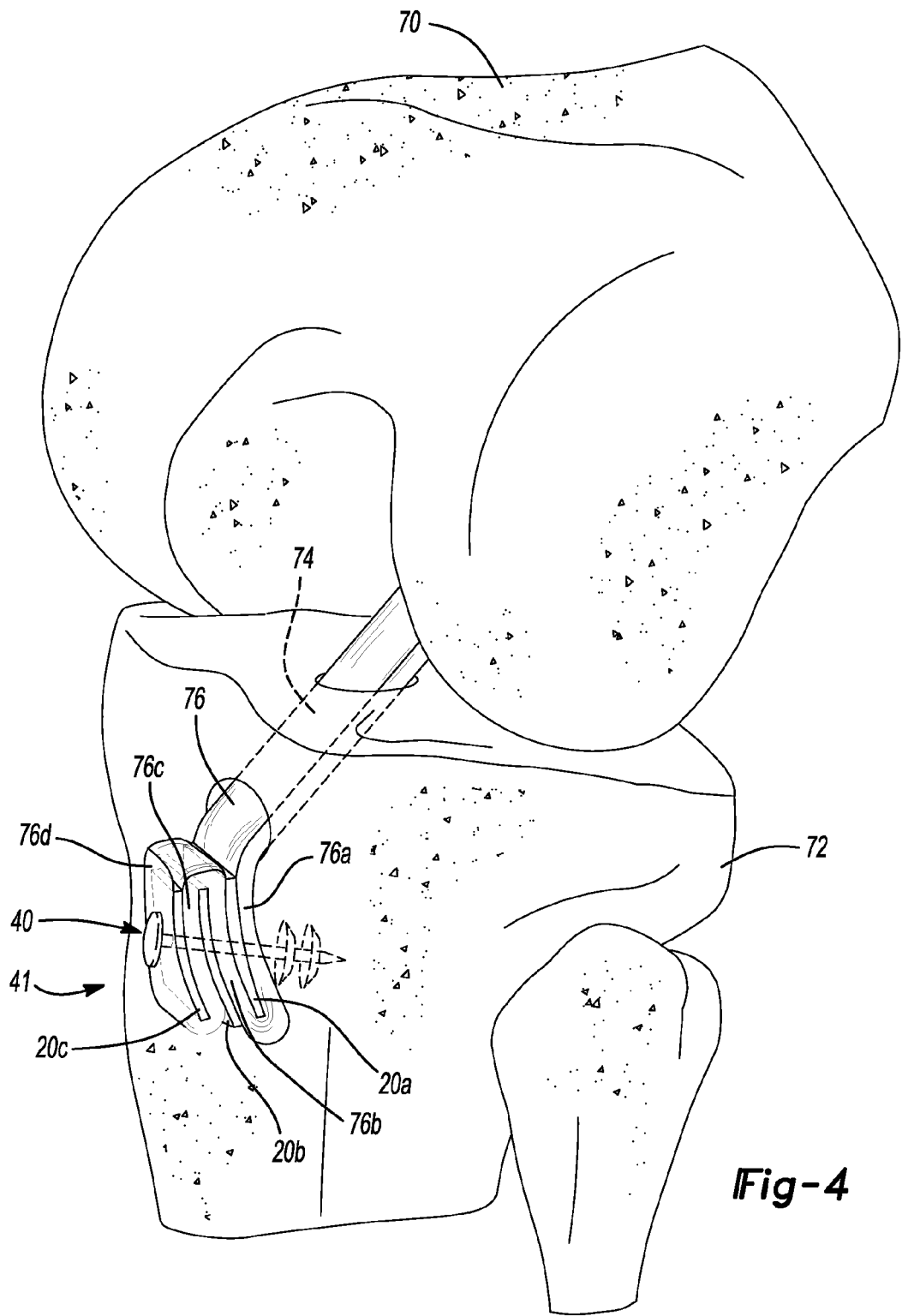
FIG. 4 is an environmental view of a second application of the friction pad, according to various embodiments.

In various procedures, a ligament, such as the ACL may be selected to be fixed to a bone, such as a tibia (FIG. 4). The ACL, and other ligaments of a human anatomy, may have an end near a natural insertion that is generally thick, tough, and appropriate for fixation to bone. After an injury and/or disease the natural fixation portion may be removed and/or damaged. Thus, the more distal portion of the ligament may be selected to be fixed to bone. The more distal portion is generally thinner and wider than the natural fixation end.

Figure 1B:
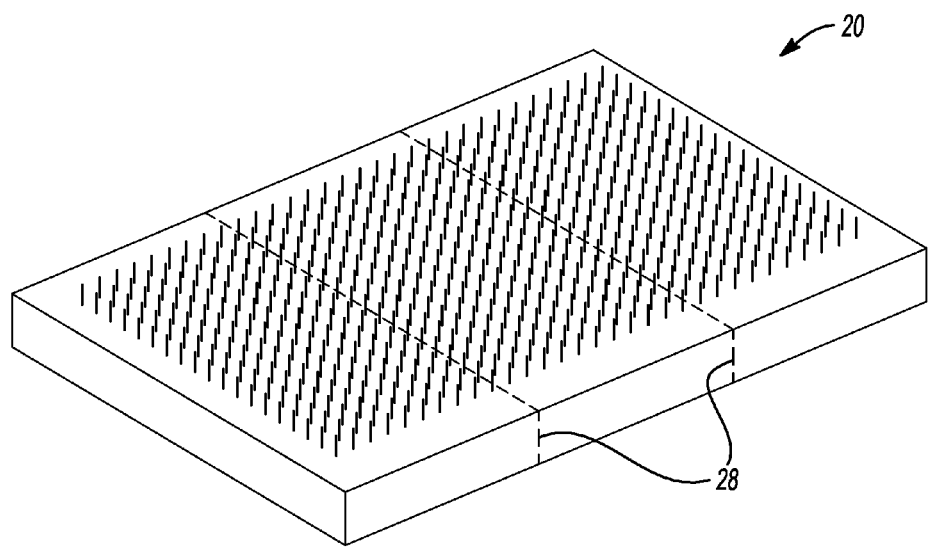
FIG. 1B is a view of a second side of the contacting or friction pad, according to various embodiments.

In various embodiments, the friction pad 20 may be provided as a large member, as illustrated in FIG. 1 B, which may have lines of perforation 28 that allow for user selection of a size by breaking, tearing, etc. along the lines of perforation. Moreover, the friction pad 20 may be formed of a material that is able to be cut by a cutting instrument such as scissors, scalpel, or other sharp instruments. This may allow the friction pad 20 to have a size selected while the pad 20 is manufactured in a single size, such as in a large sheet or member, and the user can select a size during a procedure, such as after an incision is made into a patient.

The friction pad 20 can include various friction enhancements portion that can be formed as protrusions from one or more of the surfaces 24, 26 of the friction pad 20. It is understood that the protrusions can be formed as alternating depression and protrusion portions. The protrusions can protrude from a main surface, such as the surfaces 24, 26, of the friction pad 20. The protrusions may also extend from the edge or edge surface of the pad 20. The protrusion can also be formed as a surface or edge adjacent a depression formed into the surface of the pad 20. Nevertheless the pad 20 can include protrusions or friction enhancement portions that can assist in engaging and/or increasing friction relative to a soft tissue portion.

Various protrusions can include pyramidal spikes 30, as exemplary illustrated in a selected portion of the friction pad 20. Other friction enhancement portions can include thin or right angle pyramids 32. Other friction enhancement portions can include ridged flat topped or protrusion members 34 that have a surface area that extends from the main surface of the friction pad 20. The flat top protrusion members 34 can further include a friction enhancement portion formed thereon, such as ridges or fingers. Other friction enhancement portions can include single or thin fingers 36 that extend from the main surface of the friction pad 20.

Figure 2:
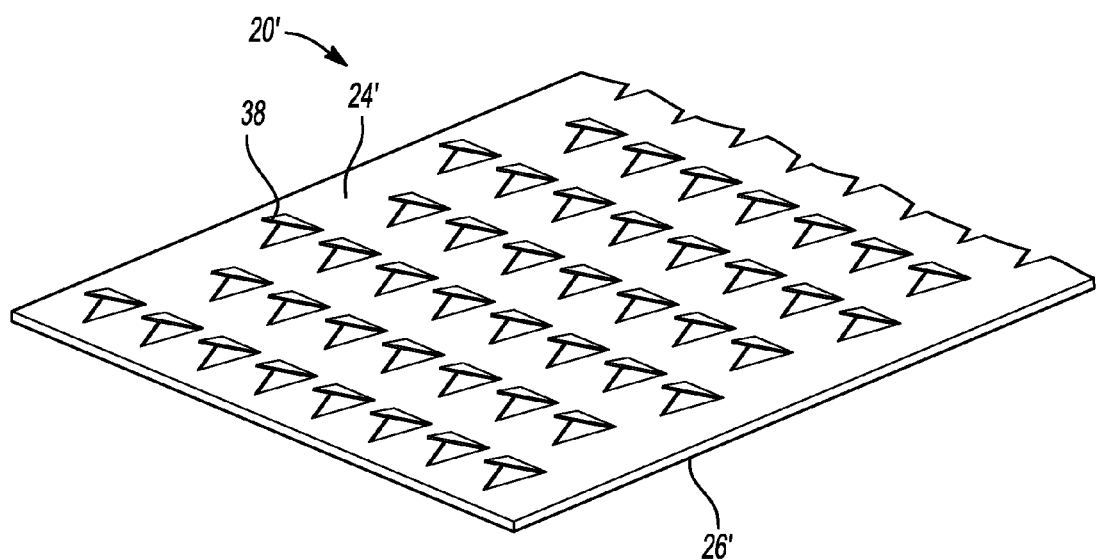
FIG. 2 is a view of a first side of a contacting or friction pad, according to various embodiments

Other selected shapes of protrusions can be included such as barbs, hooks, etc. As a further example, illustrated in FIG. 2, a fixation pad 20' is illustrated that can have opposed sides 24' and 26'. The fixation pad 20' may be formed of a metal material, including stainless steel alloys, titanium, etc. The metal material is generally selected to be biocompatible and appropriate for implantation in a subject, such as a human patient. The metal material can be worked or formed to have a thickness of about 0.1 mm to about 0.5 mm between the sides 24', 26'. The thickness may be selected or formed such that during and after implantation the pad 20' may flex to engage a bone surface thereby minimizing how far the friction pad 20' extends above the bone.

A protrusion 38 can include a pointed triangle shape that can be formed by a die that is pushed or punched through the pad 20'. The protrusion 38 can be maintained in place by the properties of the metal material of the pad 20'. The tip of the protrusion can extend about 0.1 mm to about 1 mm from the surface 24'. The protrusions 38 may also be formed by punching, machining, etching, or formed in other appropriate manners on at least one of the surfaces 24', 26' of the pad 20'. In an embodiment the protrusions 38 can be formed by chemically (e.g. photochemically) etching an area around the selected protrusion shape to form a recess into the surface 24', 26'.

The protrusions, including the fingers 36, may assist in enhancing friction or engagement relative to the soft tissue. Moreover, it is understood that the exemplarily protrusions 30-36 discussed above, can be provided over an entire area of the friction member 20 or over a small portion of the friction pad 20. Additionally, the protrusions provided in a single friction pad can all be the same type of protrusion and/or it can be selected to be of a plurality of different shapes and sizes according to a selected design or purpose.

As discussed above the friction pad 20 can include the surfaces 24 and 26 that can be positioned to engage soft tissue and/or bone of a patient. The width or thickness 22 is generally the distance between the surfaces 24 and 26. The protrusions 30-36 can extend from either one or both of the surfaces 24 or 26, as discussed above. As also discussed above, the surfaces 24 and 26 can include depressions and the protrusions are edges or surfaces adjacent to the depressions. The surfaces 24 and 26, therefore, can be provided to be positioned near soft tissue and the friction enhancement portion or portions can assist in engaging soft tissue, such as extending into the soft tissue with a smaller surface area or volume than the surface 24, 26.

Figure 3A:
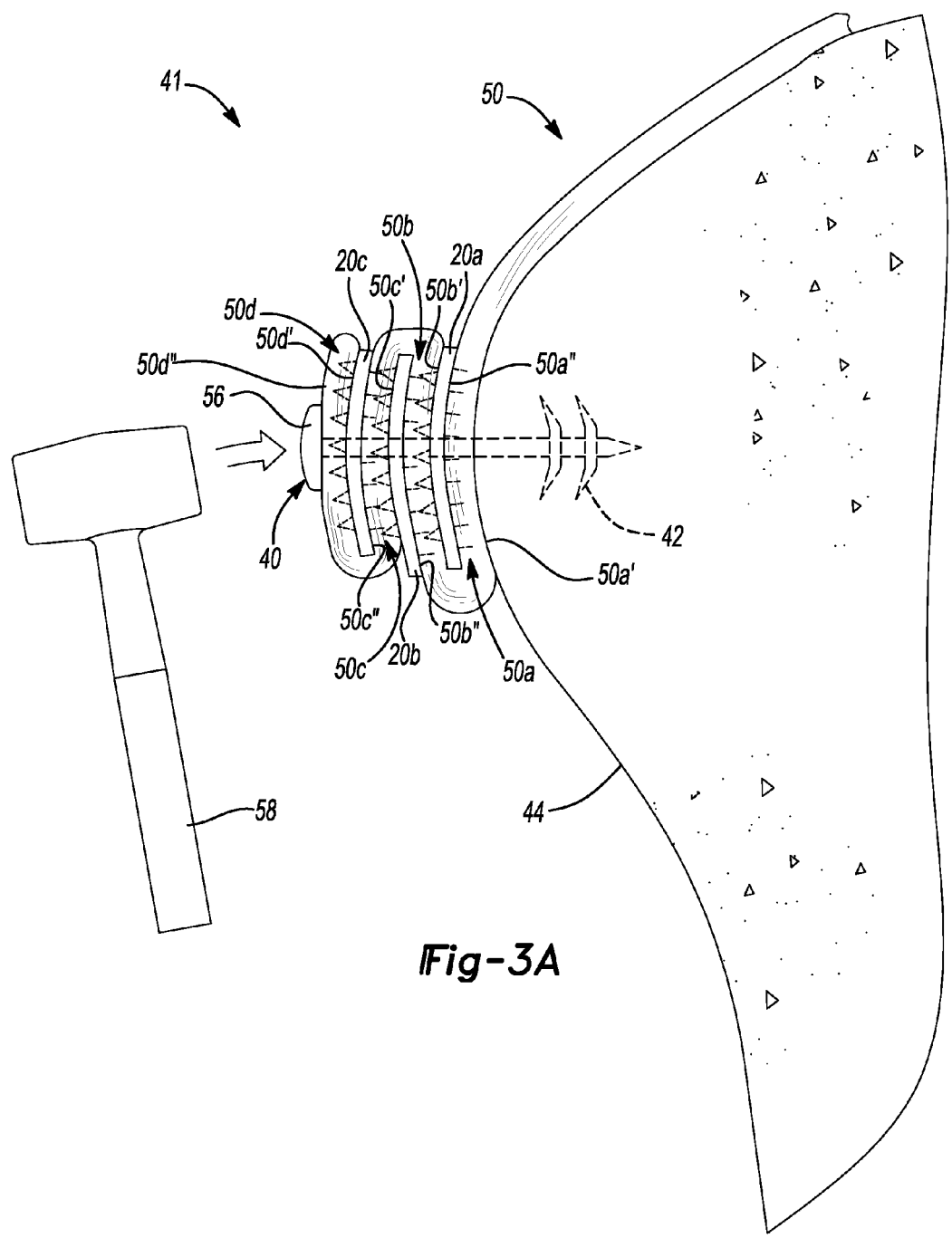
FIG. 3A is a detail environmental view of a first application of the friction pad, according to various embodiments.
Figure 3B:
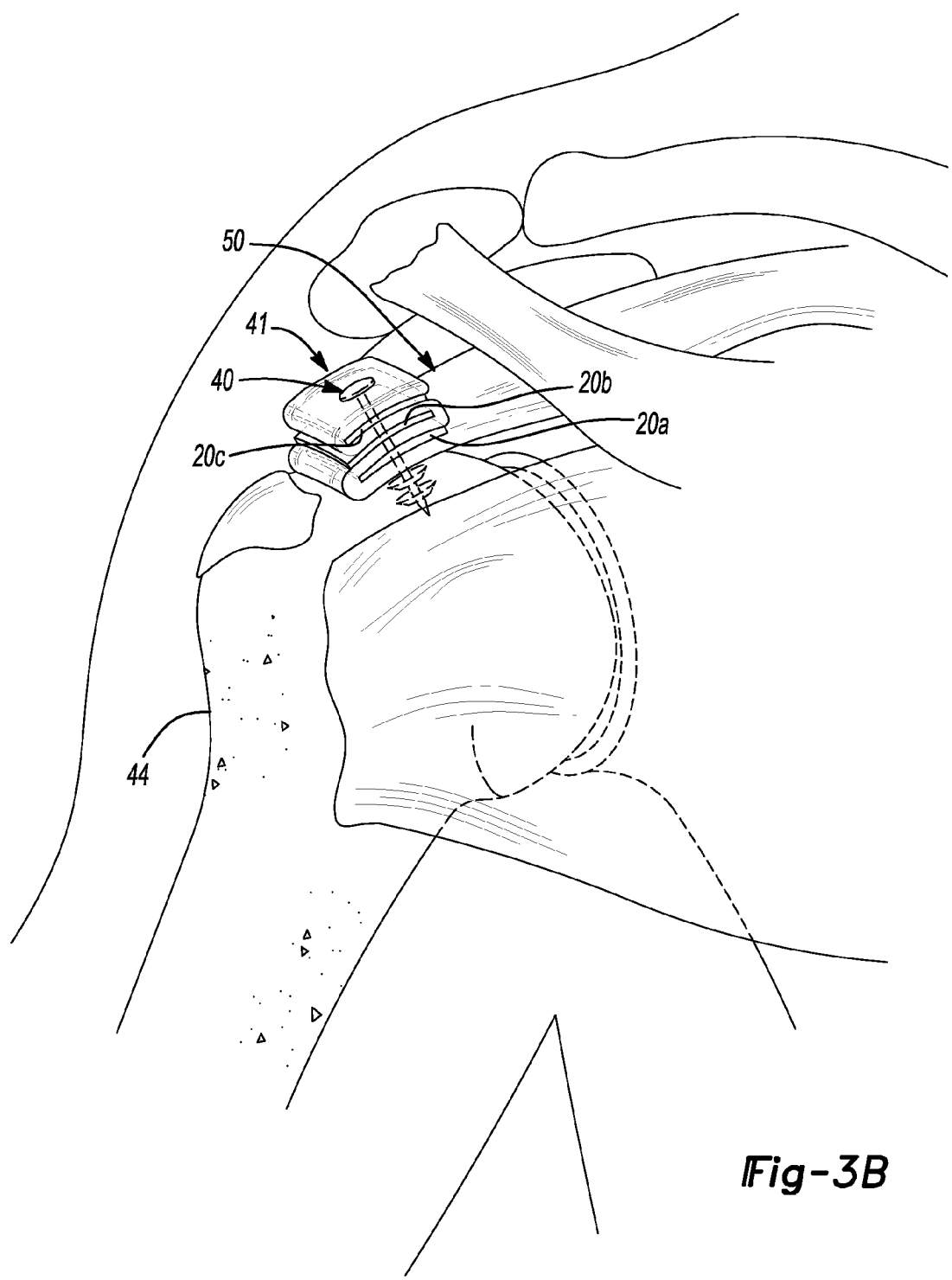
FIG. 3B is a greater environmental view of the first application of the friction pad, according to various embodiments.

With reference to FIGS. 3A and 3B, one or more of the friction pads, such as a first friction pad 20a, a second friction pad 20b, and a third friction pad 20c can be fixed with a fixation member, including a nail 40. It is understood that the three pads 20a-20c are not required. The number of pads used in a fixation area or region 41 can be selected based on the type of tissue, selected area of contact, etc. For example, the first pad 20a and the second pad 20b can be used alone and a tissue portion can be folded in a "Z"-shape as discussed further herein.

The nail 40 can include barbed portions 42 that resist movement or removal from a bone portion 44. The friction pad 20 can be used to assist in engaging or providing a surface area for contacting a soft tissue portion 50 for fixation relative to the bone portion 44. As illustrated in FIGS. 3A and 3B the soft tissue can be connected adjacent to or near a proximal end of humerus, which can be the bone portion of 44. The fixation can assist in repairing a tear of a rotator cuff to provide a fixation of soft tissue relative to the bone portion 44 to recover the natural anatomy. The soft tissue portion 40 can be naturally attached at a proximal portion of the soft tissue such as to a clavicle and or near a rib.

According to various embodiments, the friction pads 20a-20c can be positioned to be wrapped or at least partially covered by the soft tissue 50. The covering formation can include folding, such as in a "Z"-shape or overlapping configuration, as specifically illustrated in FIG. 3A. The soft tissue 50 can have a proximal connection near a center line of a patient and extend over the boney portion 44 to a fixation region where the soft tissue will be reattached. The fixation region can be selected by a user and/or selected based on the anatomy of the patient and the soft tissue.

A first portion 50*a* of the soft tissue 50 can be positioned adjacent to the bone portion 44. The first portion 50*a* can provide a first region of soft tissue. The first portion 50*a* can have a first side or region 50*a*' that contacts the bone 44 and a second side 50*a*". A friction pad, such as the first friction pad 20*a*, can have a first side, such as the side 24, positioned over the soft tissue first portion 50*a* to contact the second side 50*a*" of the first portion 50*a*. The soft tissue 50 can then be folded at a bend region over to be positioned on top the friction pad 20*a*, such as on the second side 26. The fold forms a second portion 50*b* of the soft tissue 50. The second portion may have a first side 50*b*' that contacts the second side 26 of the pad 20*a*. A second side 50*b*"of the second portion or region 50*b* opposed to the first side 50*b*' can contact a first side of the second friction pad 20*b* that may be positioned over the second region 50*b*. The soft tissue 50 can again be folded at a fold region over the friction pad 20*b* to form a third soft tissue portion or region 50*c*. A first side 50*c*' of the third region 50*c* may contact a second side of the second friction pad 20*b*. A second side 50*c*" of the third region 50*c*, opposed to the first side 50*c*', may contact a first side of the third pad 20*c*. The soft tissue can be folded over the third pad 20*c* in a fold region to form a fourth region 50*d*. A first side 50*d*' of the fourth region 50*d* may contact a second side of the pad 20*c*.

It is understood that two or three of the friction pads 20*a*, 20*b*, 20*c* are not required, but according to various embodiments can be provided. Further, a plurality including more than three of the friction pads can also be provided in the soft tissue portion 50 can be folded over the friction pads multiple times. Regardless of the number, the soft tissue 50 is generally folded over each pad provided in a generally folded or "Z" shape. Generally, the "Z"-shape or zig-zag shape will have an "open" portion or region opposite the fold portion, as illustrated in FIGS. 3A-4. Thus, the soft tissue 50 may not need to roll around the pad in the folded configuration discussed above. Further, it is understood that the friction pad can be provided as the outer most portion.

After the soft tissue 50 is folded over the friction pads, including any selected number of the friction pads 20*a*-20*c*, the nail 40 can be driven through the soft tissue regions 50*a*-50*d* and all of the friction pads 20*a*-20*c*. The nail 40 may have a head 56 that engages a second side 50*d*" opposed to the first side 50*d*' of the fourth region 50*d*. As illustrated in FIG. 3A the nail 40 can be driven through the friction pads 20*a*-20*c* and the regions of the soft tissue 50*a*-50*d* into the bone portion 44 at the fixation region 41. The pads 20-20*c* may also include a hole or bore that allows the nail 40 to pass through without piercing the pads 20*a*-20*c* while being driven therethrough. The head member or portion 56 can be driven, such as only axially, into the bone 44 with a hammer or driver 58. As discussed above, the nail portion 40, however, can be provided to engage one of the friction pads that is placed on the exterior most portion of the fixation region. Thus, the nail head 56 need not contact an outer soft tissue layer or side. The nail portion 40, may, however, be any appropriate fixation member including a screw, a barbed nail, or other member that provided to fix the soft tissue portion 50 relative to the bone portion 44.

The pads 20*a*-20*c* may include the protrusions to frictionally engage and bite into the tissue 50. It is understood, however, that the pad 20 may also be adhered to the soft tissue sides. Moreover, the fixation region 41 can be adhered to the bone 44 with appropriate adhesives. Thus, the protrusions need not be provided if the pads 20 are fixed to the tissue 50 in another manner, such as adhesive, and the nail 40 need not be used if the fixation region 41 is adhered or otherwise fixed to the bone 44.

According to various embodiments, the friction pad 20 can be provided to contact other portions of soft tissue, such as an ACL graft or portion as illustrated in FIG. 4. In FIG. 4 a femur 70 is illustrated relative to a proximal tibia 72. As is understood in the art, a tunnel 74 can be formed through the tibia 72 and a soft tissue graph 76 can be passed through the tunnel 74. The soft tissue grapht 76 can be passed over two or more, or any selected number of the friction pad 20, including only a single friction pad 20, as discussed above, three friction pads 20*a*-20*c* are illustrated in FIG. 4. Accordingly, the soft tissue 76 can include a first region 76*a*, a second region 76*b*, a third region 76*c*, and a fourth region 76*d*, similar to the regions 50*a*-50*d* discussed above. The first pad member 20A can be positioned between the first and second regions 76*a*, 76*b*; the second friction pad 20*b* can be positioned between and contact the second and third regions 76*b* and 76*c*; and the third friction pad 20*c* can be positioned between the third and fourth regions 76*c* and 76*d*. The pads 20*a*-20*c* can have sides that contact sides of the soft tissue regions 76*a*-76*d* similar to the soft tissue regions 50*a*-50*d*, as discussed above.

Again, the nail or fixation member 40 can be driven through the various regions of the soft tissue 76*a*-76*d* and the friction pads 20*a*-20*c* into the tibia 72. The fixation member 40 can include various features, such as barbed member portions, as discussed above, to assist in fixation of the nail member 40. Further, the fixation of nail member 40 can include any appropriate fixation portion such as a nail, screw, barbed nail, or the like.

The method of fixing the soft tissue can be similar to that as described above. For example, the soft tissue can be a torn portion of a natural soft tissue portion. The soft tissue portion can be tensioned to an appropriate amount and affixed to a boney member, near or adjacent the first boney member, where a natural insertion of the soft tissue occurs. For example, a number of the pads can be selected to achieve a desired tension. The torn portion or region of the soft tissue can be folded to encapsulate and/or at least partially cover the friction pad, as discussed above. Moreover, a graft, for example is illustrated in FIG. 4, can be provided to connect to bone portions, including the femur 70 and the tibia 72. As is understood in the art, the graft 76 can be fixed to a second bone portion with the friction pad system as discussed above, or with other appropriate fixation members, such as the EZLoc® soft tissue fixation device sold by Biomet, Inc. The friction pad 20 can be used to fix a second end of the tissue portion, such as the graft 76, at a second end, such as to the tibia 72 as discussed above.

The soft tissue graft or portion can be overlapped or folded over one or more of the friction pads 20 to provide for a larger surface area for contacting soft tissue at the fixation region 41. The larger surface area can resist tearing, removal, or splitting of the soft tissue portion and/or graft when fixed with a fixation member, such as the nail 40. Accordingly, the friction pad 20 can provide further or additional surface area for contacting the soft tissue portions when or while the fixation member, including the nail 40, is driven through the soft tissue and the friction pad 20. Therefore the friction pad 20 can resist pull-out or pull-away from the fixation member 40 after implementation and fixation to the bone portion 44. The friction pads can provide longevity and/or immediate fixation strength relative to the soft tissue. Thus, the friction pads can enhance fixation of the soft tissue relative to the bone portion. The friction pads, as discussed above, can be formed from materials that assist in providing longevity or enhanced fixation with the fixation member 44 that can enhance or augment fixation of the soft tissue with the fixation member 40 relative to the boney portions.

According to the various embodiments, the pads 20, 20' may be used to reinforce and enhance pull-out strength of various soft tissues or soft tissue portions. As discussed above, the pads 20, 20' can be used to form the fixation region for attachment to bone. The pads 20, 20'can contact the soft tissue and be held fixedly in place, such as with the protrusions, for fixation to the bone. The fixation region can be fixed to bone with the nail 40 or other appropriate fixation member. Further, the folding and/or numerous pads 20, 20' in the fixation region 41 can allow for selected tensions of the soft tissue portion 50 without cutting or shortening the tissue 50.

With reference to FIGS. 5A and 5B, a soft tissue portion 100 is illustrated. The soft tissue portion 100 includes at least two regions including a first narrow and/or thicker region 102 and a broad and/or thin region 104. The thicker region 102 can be nearer an insertion region or point while the broad and thinner region 104 can be nearer a tear or position for fixation of the ligament portion 100. The ligament 100 can be prepared for fixation to a bone portion 110, as illustrated in FIG. 5B, with the use of one or more of a friction or fixation pad 120 including at least the friction pad 120. More than one friction pad can be selected, including at least a second friction pad 122 and a third friction pad 124. Each of the friction pads can include a structure on at least one surface. The structure can include the friction enhancement features, including at least one or more teeth or raised regions 130 formed or extending from a surface to the friction pads 120-124.

The friction pads 120-124, or any appropriate number thereof, can be positioned on the thinner and broader region 104 of the ligament 100. As illustrated in FIGS. 5A and 5B, the respective friction pads can be positioned on a surface of the ligament 100, such as in a region near a first side of the broad and thin region 104. The ligament portion 104 can then be rolled in a direction, such as in the direction of arrow 140. After each turn of the broad ligament region 104 that exposes a surface or portion that is not contacting a friction pad, a further friction pad can be positioned on the exposed surface, and the rolling can continue in the direction of arrow 140. The broaden region 104 of the ligament 100 can continue to be rolled and turned until a bundle or fixation region 150 of the broaden region 104 and the one or more friction pads 120-124 is formed. The fixation region 150 including the friction pads 120-124 can be fixed to the bone portion and/or region 110 with a fixation member, including the nail 40 illustrated and discussed above. The nail 40 can include a taper or barbed portion 42 and a contacting or fixation head 56. The fixation head 56 can contact one or more of the friction pads, such as the friction pad 124, or directly contact the ligament 100 as illustrated in FIG. 5B.

Accordingly the ligament 100, or any other appropriate soft tissue region, can be prepared with one or more of the friction pads 120-124 to be fixed to the bone portion 100. As illustrated and discussed above, the friction pads 120-124 can form or assist in enhancing a region to be fixed to the bone portion 110. The friction pads 120-124 can include features and/or can be formed of materials similar to those discussed above for the friction pads. The friction pads 120-124 can assist in resisting removal or tear through of the soft tissue from the fixation member including the nail 40.

The friction pads 120-124 can include surfaces that contact the soft tissue surfaces to assistance in ensuring fixation of the friction pad relative to the soft tissue. Moreover, the friction pads 120-124 can include features, including the raised regions 130, which may engage and contact the soft tissue to ensure fixation of the friction pads 120-124 relative to the soft tissue surfaces.

Figure 6A:
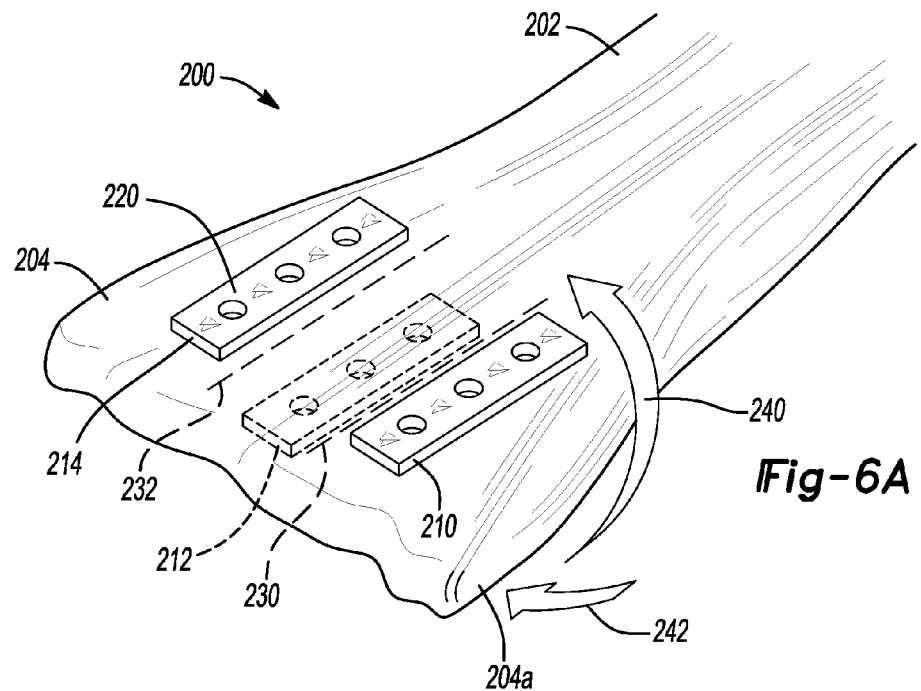
FIG. 6A is a detail view of a soft tissue portion and three friction pads.
Figure 6B:
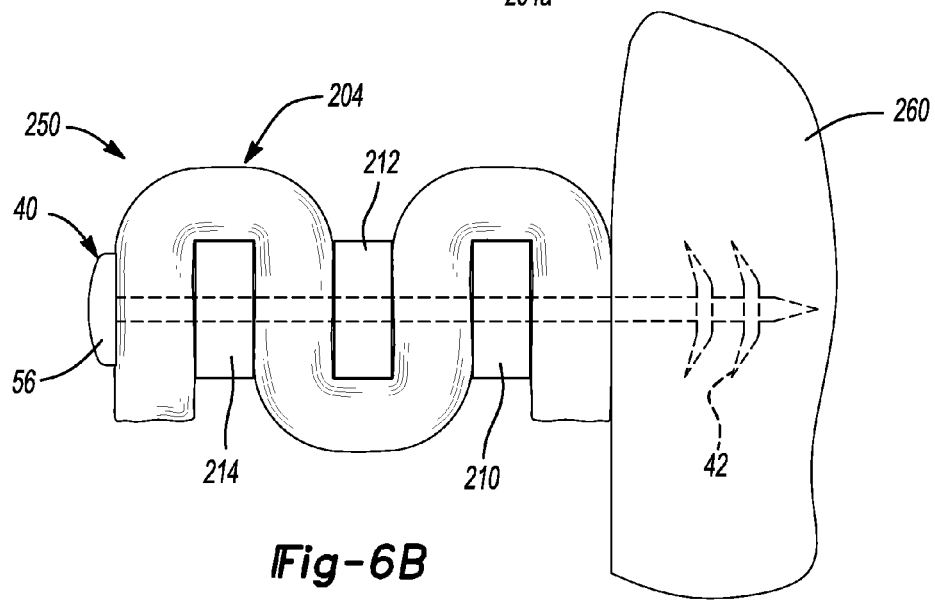
FIG. 6B is a detail view of a portion of a fixation region of a soft tissue with friction pads, according to various embodiments.

Turning references to FIGS. 6A and 6B, a soft tissue portion 200 is illustrated, including a ligament or other soft tissue potion. The soft tissue portion 200 can include regions similar to the soft tissue portion 100 illustrated in FIG. 5A including a thick region 202 that is generally thicker and narrower than a flattened thin region 204. The flattened thin region 204 can have a width that is greater than the width of the thick region 202, but is generally a substantially thinner. The thin region 204 can be made to engage or be positioned adjacent to friction pads 210, 212 and 214. The friction pads 210-214 can include surface features, including raised points and friction enhancement regions 220, such as those discussed above. The friction enhancement regions 220 can assist in engaging the soft tissue 200 to resist movement to the friction pad 210-214 relative to the soft tissue.

The friction pads 210-212 can be positioned on or in the thin region 204 such that the thin region 204 can be folded, including in a fan fold or creasing manner, relative to the friction pads 210-214. As illustrated in FIG. 6A, fold areas 230 and 232 can be defined by the soft tissue 200 such that the soft tissue can be folded near or at the fold or crease areas 230, 232 to at least partially or totally surround the friction pads 210-214. For example, a first edge 204a of the thin region 204 can be folded generally in the direction of arrow 240 over the friction pad 210. The folded region, including the edge 204a over the friction pad 210 can then be folded back in the direction of arrow 242 to cover or contact a surface of the friction pad 212.

After fan folding the thin region 204 back and forth in this manner, the thin region 204 can form a fixation region 250, as illustrated in FIG. 6B. The fixation region 250 can be fixed to a bone portion 260 that can be any appropriate bone portion, including any of those discussed above. The fixation region 250 can include the friction pads 210-214 that are completely or substantially surrounded by the soft tissue thin region 204. A fixation member, such as the nail 40, can be used to fix the fixation region 250 relative to the bone in 260. Again, the nail 40 can include a head 56 that can contact soft tissue portion 204 and various bone fixation enhancement regions, such as the barb 42 to enhance fixation to the bone portion 260.

The soft tissue portion 200 can then be fixed to the bone 260 at the fixation region 250. The fixation region 250 can be enhanced with the friction pads 210-214 to assist in resisting pull through or tearing of the soft tissue after fixation with the fixation member 40. Again, it is understood, that the friction pads 210-214 can be formed to include features including those discussed above and illustrated and can also be formed of similar materials to the friction pads discussed above. For example, the friction pads 210-214 can be formed of a metal or metal alloy and the friction enhancement portions 220 can be formed from the friction pads 210-214, such as by punching. Moreover, the friction pads 210-214 can be placed within folds of the soft tissue region 204. Accordingly the soft tissue can be enhanced for fixation relative to a bone portion with a fixation member, including the nail 40, to assist in maintaining and/or securing fixation of soft tissue to a bone portion in a selective procedure.

It is understood that the various exemplary embodiments can include features in combination, though not exemplarily shown together. For example, the friction pads, according to various embodiments, may be formed and/or designed to bend and/or conform to a bone portion to minimize a thickness of a fixation region that includes the friction pads. Also, according to various embodiments, friction enhancement portions (e.g. 30, 32, 34, 36, 38, 130, 220) may be formed on two or more sides of each respective friction pad. For example, a die can be formed to punch alternating members or fingers on opposite sides of the friction pad.

The foregoing description of the embodiments has been provided for purposes of illustration and description. It is not intended to be exhaustive or to limit the disclosure. For example, generally the soft tissue or portion thereof can be manipulated to contact a friction pad, according to various embodiments. The manipulation can include folding, rolling, creasing, etc. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

What is claimed is:

1. A method of fixing a soft tissue portion to an anatomical portion, comprising:
    selecting a first end of the soft tissue portion;
    extending a first region of the first end of the soft tissue portion over a portion of the anatomical portion;
    contacting a first surface of a first member adjacent the first region so that the first surface of the first member faces the anatomical portion;
    manipulating at least a first portion of the first end of the soft tissue portion over the first member to contact a second surface of the first member with a second region of the first end of the soft tissue portion so that the second surface of the first member opposes the first surface of the first member and faces away from the anatomical portion; and
    driving a second member through the first region, the second region, and the first member and into the anatomical portion.

2. The method of claim 1, further comprising:
    contacting a third surface of a third member with the second region of the first end of the soft tissue portion; and
    folding the first end of the soft tissue portion over the first member to contact a fourth surface of the second member with a third region of the first end of the soft tissue portion.

3. The method of claim 2, further comprising:
    driving the second member through the first region, the second region, the first member, the third member and the third region of the first end of the soft tissue portion and into the anatomical portion.

4. The method of claim 1, wherein manipulating at least the first portion of the first end of the soft tissue portion over the first member to contact the second surface of the first member with the second region of the first end of the soft tissue portion includes at least one of rolling the first end, folding the first end, or creasing the first end.

5. A method of fixing a soft tissue portion to an anatomical portion, comprising:
    placing a first portion of a first end of the soft tissue portion having a first length over a bone portion of the anatomical portion;
    contacting a first surface of a first fixation member to a first region of the first portion;
    manipulating the first portion of the soft tissue portion over the first fixation member to contact a second surface of the first fixation member that is opposite and facing away from the first surface with a second region of the first portion of the soft tissue portion such that the first portion of the soft tissue portion at least partially surrounds the first member;
    contacting a third surface of a second fixation member to a third region of the first portion;
    manipulating the first portion of the soft tissue portion over the second fixation member to contact a fourth surface of the second fixation member that is opposite the third surface with a fourth region of the first portion of the soft tissue portion such that the first portion of the soft tissue portion at least partially surrounds the second member; and
    connecting all of the first region, the second region, the third region, the fourth region, the first member, and the second fixation member to the bone portion;
    wherein the first region, the second region, the third region, the fourth region, the first member, and the second member form a fixation region where the soft tissue portion is folded around the first fixation member and the second fixation member.

6. The method of claim 5, wherein connecting all of the first region, the second region, the third region, the fourth region, the first member, and the second member to the bone portion includes driving a third member through all of the first region, the second region, the third region, the fourth region, the first fixation member and the second fixation member into the bone portion.

7. The method of claim 6, further comprising providing the third member with bone fixation barbs.

8. The method of claim 6, wherein driving the third member through all of the first region, the second region, the third region, the fourth region, the first member, and the second fixation member into the bone portion includes only axially driving the third member into the bone portion.

9. The method of claim 5, wherein contacting the first surface of the first fixation member to the first region of the first portion and contacting the third surface of the second fixation member to the third region of the first portion includes frictionally engaging the first region with the first fixation member and frictionally engaging the second region with the second fixation member.

10. The method of claim 5, further comprising:
    providing both the first member and the second member as a polymer material.

11. The method of claim 5, further comprising:
    providing both the first member and the second member formed of a metal material.

12. The method of claim 11, further comprising: providing a first protrusion extending from a first surface of the first fixation member and a second protrusion extending from a second surface of the second fixation member.

13. The method of claim 5, further comprising:
forming a fixation region by:
manipulating the first portion of the soft tissue portion over the first fixation member to contact a second surface of the first fixation member that is opposite the first surface with a second region of the first portion of the soft tissue portion such that the first portion of the soft tissue portion at least partially surrounds the first fixation member,
contacting the third surface of the second fixation member to the third region of the first portion, and
manipulating the first portion of the soft tissue portion over the second fixation member to contact the fourth surface of the second fixation member that is opposite the third surface with the fourth region of the first portion of the soft tissue portion such that the first portion of the soft tissue portion at least partially surrounds the second fixation member;
wherein the fixation region is in a substantially "Z"-shape fold of the soft tissue portion.

\* \* \* \* \*

UNITED STATES PATENT AND TRADEMARK OFFICE
CERTIFICATE OF CORRECTION

PATENT NO. : 9,433,493 B2
APPLICATION NO. : 14/071331
DATED : September 6, 2016
INVENTOR(S) : Mark V. Vandewalle It is certified that error appears in the above-identified patent and that said Letters Patent is hereby corrected as shown below:

In the Claims

In Column 11, Line 1, in Claim 12, after "comprising:", insert --¶--, therefor

Signed and Sealed this
Sixth Day of March, 2018

Andrei Iancu
*Director of the United States Patent and Trademark Office*